United States Patent
Kramer

(10) Patent No.: US 7,385,043 B1
(45) Date of Patent: Jun. 10, 2008

(54) HOMOGENEOUS MULTIPLEX SCREENING ASSAYS AND KITS

(75) Inventor: Fred R. Kramer, Riverdale, NY (US)

(73) Assignee: The Public Health Research Institute of the City of New York, Inc., Newark, NJ (US)

(*) Notice: Subject to any disclaimer, the term of this patent is extended or adjusted under 35 U.S.C. 154(b) by 576 days.

(21) Appl. No.: 10/426,556

(22) Filed: Apr. 30, 2003

(51) Int. Cl.
*C12Q 1/68* (2006.01)
*C07H 15/12* (2006.01)

(52) U.S. Cl. .................. 536/23.1; 536/22.1; 435/6

(58) Field of Classification Search ............ None
See application file for complete search history.

(56) References Cited

U.S. PATENT DOCUMENTS

| | | | | |
|---|---|---|---|---|
| 6,007,994 | A | * | 12/1999 | Ward et al. ............. 435/6 |
| 6,150,097 | A | * | 11/2000 | Tyagi et al. ............ 435/6 |
| 6,627,748 | B1 | * | 9/2003 | Ju et al. .............. 536/25.32 |
| 6,738,502 | B1 | * | 5/2004 | Coleman et al. ........ 382/133 |
| 2005/0112595 | A1 | * | 5/2005 | Zhao et al. ............ 435/6 |
| 2005/0287526 | A1 | * | 12/2005 | Landegren et al. ...... 435/6 |

FOREIGN PATENT DOCUMENTS

WO WO 00/65094 11/2000

OTHER PUBLICATIONS

Lee LG et al. "Seven color homogeneous detection of six PCR products", Biotechniques, 1999, vol. 27, No. 2, p. 342-349.*
Han M, et al. "Quantum-dot-tagged microbeads for multiplexed optical coding of biomolecules", Nature Biotechnology, 2001, vol. 19, p. 631-635.*
Ried T, et al. "Simultaneous visualization of seven different DNA probes by in situ hybridization using combinatorial fluorescence and digital imaging microscopy", PNAS, 1992, vol. 89, p. 1388-1392.*
Tyagi et al. "Wavelength shifting molecular beacons", Nature Biotechnology, vol. 18, p. 1191-1196.*
Bernard PS et al. "Homogeneous multiplex genotyping of hemochromatosis mutations with fluorescent hybridization probes", American Journal of Pathology, 1998, vol. 153, No. 4, p. 1055-1061.*
Vet Jam, et al. Multiplex detection of four pathogenic retroviruses using molecular beacons, PNAS, 1999, vol. 96, p. 6394-6399.*
El-Hajj, H. et al. (2001), Detection of Rifampin Resistance in *Mycobacterium tuberculosis* in a Single Tube with Molecular Beacons, J. Clin. Microbiol. 39: 4131-4137.
Espy, M.J. et al. (2002), Detection of Vaccinia Virus, Herpes Simplex Virus, Varicella-Zoster Virus, and *Bacillus anthracis* by LightCycler Polymerase Chain Reaction after Autoclaving: Implications for Biosafety of Bioterrorism Agents, Mayo Clin. Proc. 77: 624-628.

(Continued)

*Primary Examiner*—Gary Benzion
*Assistant Examiner*—Stephanie K. Mummert
(74) *Attorney, Agent, or Firm*—Synnestvedt & Lechner LLP

(57) ABSTRACT

Highly multiplexed homogeneous in vitro screening assays for numerous possible nucleic acid targets, any of which might be present in a sample, utilize fluorescent hybridization probes that are combinatorially coded from a panel of fluorophores by subdividing each probe into portions and differently labeling each portion such that, when portions are combined, each probe has a unique code. The assays may include target amplification and real-time detection. Probe sets and kits containing additional assay reagents may be used to perform the screening assays.

12 Claims, 9 Drawing Sheets

OTHER PUBLICATIONS

Gingeras, T.R. et al. (1998), Simultaneous Genotyping and Species Identification Using Hybridization Pattern Recognition Analysis of Generic *Mycobacterium* DNA Arrays. Genet. Res. 8: 435-448.

Han, et al. (2001), Quantum-Dot-Tagged Microbeads for Multiplexed Optical Coding of Biomolecules, Nature Biotechnol. 19, 631-635.

Hirsch, M.S. et al. (1998), Antiretroviral Drug Resistance testing in Adults with HIV Infection, JAMA 279: 1984-199.

Lee, L.G., et al. (1999), Seven-Color, Homogeneous Detection of Six PCR Products, BioTechniques, 27: 342-349.

Levsky, J.M. et al. (2002), Single-Cell Gene Expression Profiling, Science 297: 836-840.

Li Qingge et al., (2002), A new class of homogeneous nucleic acid probes based on specific displacement hybridization, Nucleic Acids Research 30: 2 e5.

Livak, K.J. et al. (1995), Oligonucleotides with fluorescent Dyes at Opposite Ends Provide a Quenched Probe System Useful for Detecting PCR Product and Nucleic Acid Hybridization, PCR Meth. Appl. 4: 357-362.

Piatek, et al. (1998), Molecular beacon sequence analysis for detecting drug resistance in *Mycobacterium tuberculosis*, Nature Biotechnology, 16: 359-363.

Schena, M. et al. (1995), Quantitative Monitoring of Gene Expression Patterns with a Complementary DNA Microarray, Science 20: 467-470.

Speicher et al., (1996), Karyotyping Human Chromosomes by Combinatorial Multi-fluor FISH, Nature Genet. 12: 368-375.

Tong, A.K. et al. (2001), Combinatorial Fluorescence Energy Transfer Tags for Multiplex Biological Assays, Nature Biotechnol. 19: 756-759.

Tyagi, S. and Kramer, F.R. (1996), Molecular Beacons: Probes that Fluoresce upon Hybridization, Nature Biotechnol. 14: 303-308.

Tyagi, S. et al. (1998), Multicolor Molecular Beacons for Allele Discrimination, Nature Biotechnol. 16: 49-53.

Tyagi. S. et al. (1998), supra; Vet, J.A. et al. (1999), Multiplex Detection of Four Pathogenic Retroviruses Using Molecular Beacons, Proc. Natl. Acad. Sci. USA 96: 6394-6399.

Ohnishi, Yozo et al. (2001), A high-throughput SNP typing system for genome-wide association studies, Journal of Human Genetics 2001, vol. 46:471-477.

Tyagi et al. "Wavelength shifting molecular beacons", Nature Biotechnology, 2000 vol. 18, p. 1191-1196.

* cited by examiner

TWO COLORS PER PROBE:
PANEL OF 4(a, b, c, d), 5(+e), 6(+f), 7(+g) or 8(+h) FLUOROPHORES

```
ab                                  }= 6    }       }       }       }
ac    bc                            }       }       }       }       }
ad    bd    cd                      }       }= 10   }       }       }
                                            }       }       }       }
ae    be    ce    de                }       }       }= 15   }       }
                                                    }       }       }
af    bf    cf    df    ef                          }       }= 21   }
                                                            }       }
ag    bg    cg    dg    eg    fg                            }       }= 28
                                                                    }
ah    bh    ch    dh    eh    fh    gh                              }
```

THREE COLORS PER PROBE:
PANEL OF 5(a, b, c, d, e), 6(+f), 7(+g) or 8(+h) FLUOROPHORES

```
abc                             }= 10    }       }       }
abd                             }        }       }       }
abe                             }        }       }       }
acd    bcd                      }        }       }       }
ace    bce                      }        }       }       }
ade    bde    cde               }        }       }       }
                                         }= 20   }       }
abf                                      }       }       }
acf    bcf                               }       }       }
adf    bdf    cdf                        }       }       }
aef    bef    cef    def                 }       }       }
                                                 }= 35   }
abg                                              }       }
acg    bcg                                       }       }
adg    bdg    cdg                                }       }
aeg    beg    ceg    deg                         }       }
afg    bfg    cfg    dfg    efg                  }       }
                                                         }
abh                                                      }
ach    bch                                               }= 56
adh    bdh    cdh                                        }
aeh    beh    ceh    deh                                 }
afh    bfh    cfh    dfh    efh                          }
agh    bgh    cgh    dgh    egh    fgh                   }
```

FIGURE 1

FIRST TERNARY COLOR CODEBOOK

|        | 0(abc)      | 1(abd)      | 2(abe)      | 3(acd)      | 4(ace)      |
|--------|-------------|-------------|-------------|-------------|-------------|
| 0(abc) |             | 0+1(abcd)   | 0+2(abce)   | 0+3(abcd)   | 0+4(abce)   |
| 1(abd) | 0+1(abcd)   |             | 1+2(abde)   | 1+3(abcd)   | 1+4(abcde)  |
| 2(abe) | 0+2(abce)   | 1+2(abde)   |             | 2+3(abcde)  | 2+4(abce)   |
| 3(acd) | 0+3(abcd)   | 1+3(abcd)   | 2+3(abcde)  |             | 3+4(acde)   |
| 4(ace) | 0+4(abce)   | 1+4(abcde)  | 2+4(abce)   | 3+4(acde)   |             |
| 5(ade) | 0+5(abcde)  | 1+5(abde)   | 2+5(abde)   | 3+5(acde)   | 4+5(acde)   |
| 6(bcd) | 0+6(abcd)   | 1+6(abcd)   | 2+6(abcde)  | 3+6(abcd)   | 4+6(abcde)  |
| 7(bce) | 0+7(abce)   | 1+7(abcde)  | 2+7(abce)   | 3+7(abcde)  | 4+7(abce)   |
| 8(bde) | 0+8(abcde)  | 1+8(abde)   | 2+8(abde)   | 3+8(abcde)  | 4+8(abcde)  |
| 9(cde) | 0+9(abcde)  | 1+9(abcde)  | 2+9(abcde)  | 3+9(acde)   | 4+9(acde)   |

|        | 5(ade)      | 6(bcd)      | 7(bce)      | 8(bde)      | 9(cde)      |
|--------|-------------|-------------|-------------|-------------|-------------|
| 0(abc) | 0+5(abcde)  | 0+6(abcd)   | 0+7(abce)   | 0+8(abcde)  | 0+9(abcde)  |
| 1(abd) | 1+5(abde)   | 1+6(abcd)   | 1+7(abcde)  | 1+8(abde)   | 1+9(abcde)  |
| 2(abe) | 2+5(abde)   | 2+6(abcde)  | 2+7(abce)   | 2+8(abde)   | 2+9(abcde)  |
| 3(acd) | 3+5(acde)   | 3+6(abcd)   | 3+7(abcde)  | 3+8(abcde)  | 3+9(acde)   |
| 4(ace) | 4+5(acde)   | 4+6(abcde)  | 4+7(abce)   | 4+8(abcde)  | 4+9(acde)   |
| 5(ade) |             | 5+6(abcde)  | 5+7(abcde)  | 5+8(abde)   | 5+9(acde)   |
| 6(bcd) | 5+6(abcde)  |             | 6+7(bcde)   | 6+8(bcde)   | 6+9(bcde)   |
| 7(bce) | 5+7(abcde)  | 6+7(bcde)   |             | 7+8(bcde)   | 7+9(bcde)   |
| 8(bde) | 5+8(abde)   | 6+8(bcde)   | 7+8(bcde)   |             | 8+9(bcde)   |
| 9(cde) | 5+9(acde)   | 6+9(bcde)   | 7+9(bcde)   | 8+9(bcde)   |             |

FIGURE 6a

SECOND TERNARY COLOR CODEBOOK

|        | 9(abc)      | 8(abd)      | 7(abe)      | 6(acd)      | 5(ace)      |
|--------|-------------|-------------|-------------|-------------|-------------|
| 9(abc) |             | 8+9(abcd)   | 7+9(abce)   | 6+9(abcd)   | 5+9(abce)   |
| 8(abd) | 8+9(abcd)   |             | 7+8(abde)   | 6+8(abcd)   | 5+8(abcde)  |
| 7(abe) | 7+9(abce)   | 7+8(abde)   |             | 6+7(abcde)  | 5+7(abce)   |
| 6(acd) | 6+9(abcd)   | 6+8(abcd)   | 6+7(abcde)  |             | 5+6(acde)   |
| 5(ace) | 5+9(abce)   | 5+8(abcde)  | 5+7(abce)   | 5+6(acde)   |             |
| 4(ade) | 4+9(abcde)  | 4+8(abde)   | 4+7(abde)   | 4+6(acde)   | 4+5(acde)   |
| 3(bcd) | 3+9(abcd)   | 3+8(abcd)   | 3+7(abcde)  | 3+6(abcd)   | 3+5(abcde)  |
| 2(bce) | 2+9(abce)   | 2+8(abcde)  | 2+7(abce)   | 2+6(abcde)  | 2+5(abce)   |
| 1(bde) | 1+9(abcde)  | 1+8(abde)   | 1+7(abde)   | 1+6(abcde)  | 1+5(abcde)  |
| 0(cde) | 0+9(abcde)  | 0+8(abcde)  | 0+7(abcde)  | 0+6(acde)   | 0+5(acde)   |

|        | 4(ade)      | 3(bcd)      | 2(bce)      | 1(bde)      | 0(cde)      |
|--------|-------------|-------------|-------------|-------------|-------------|
| 9(abc) | 4+9(abcde)  | 3+9(abcd)   | 2+9(abce)   | 1+9(abcde)  | 0+9(abcde)  |
| 8(abd) | 4+8(abde)   | 3+8(abcd)   | 2+8(abcde)  | 1+8(abde)   | 0+8(abcde)  |
| 7(abe) | 4+7(abde)   | 3+7(abcde)  | 2+7(abce)   | 1+7(abde)   | 0+7(abcde)  |
| 6(acd) | 4+6(acde)   | 3+6(abcd)   | 2+6(abcde)  | 1+5(abcde)  | 0+6(acde)   |
| 5(ace) | 4+5(acde)   | 3+5(abcde)  | 2+5(abce)   | 1+5(abcde)  | 0+5(acde)   |
| 4(ade) |             | 3+4(abcde)  | 2+4(abcde)  | 1+4(abde)   | 0+4(acde)   |
| 3(bcd) | 3+4(abcde)  |             | 2+3(bcde)   | 1+3(bcde)   | 0+3(bcde)   |
| 2(bce) | 2+4(abcde)  | 2+3(bcde)   |             | 1+2(bcde)   | 0+2(bcde)   |
| 1(bde) | 1+4(abde)   | 1+3(bcde)   | 1+2(bcde)   |             | 0+1(bcde)   |
| 0(cde) | 0+4(acde)   | 0+3(bcde)   | 0+2(bcde)   | 0+1(bcde)   |             |

FIGURE 6b

HOMOGENEOUS MULTIPLEX SCREENING ASSAYS AND KITS

TECHNICAL FIELD

This invention relates to homogenous in vitro multiplexed assays, including particularly homogeneous amplification assays, for screening biological samples for the presence of any of a large number of nucleic acid sequences.

BACKGROUND

A variety of assay techniques are available for testing a biological sample obtained from any of a variety of sources for the presence of a nucleic acid sequence that may indicate the presence, for example, of a particular bacterium, virus or other pathogen, including a particular strain or mutant. Assays are also available for testing such samples for the presence of a nucleic acid sequence of the subject's own genomic DNA that may indicate the presence, for example, of one or another disease-related genetic mutation. Assays may include oligonucleotide probes bearing detectable labels, for example, $P^{32}$ or fluorophores. Nucleic acids, either DNA or RNA, in a sample may be probed directly. Alternatively, assays may include amplification of target sequences by any of several amplification techniques, for example, PCR, NASBA or TMA. Amplification assays may be monitored in real time utilizing intercalating dyes, for example SYBR green, or fluorescently labeled probes, such as 5' nuclease probes Livak, K. J. et al. (1995), Oligonucleotides with fluorescent Dyes at Opposite Ends Provide a Quenched Probe System Useful for Detecting PCR Product and Nucleic Acid Hybridization, PCR Meth. Appl. 4: 357-362, dual FRET probes, Espy, M. J. et al. (2002), Detection of Vaccinia Virus, Herpes Simplex Virus, Varicella-Zoster Virus, and *Bacillus anthracis* by LightCycler Polymerase Chain Reaction after Autoclaving: Implications for Biosafety of Bioterrorism Agents, Mayo Clin. Proc. 77: 624-628, or molecular beacon probes, Tyagi, S. and Kramer, F. R. (1996), Molecular Beacons: Probes that Fluoresce upon Hybridization, Nature Biotechnol. 14: 303-308; Tyagi, S. et al. (1998), Multicolor Molecular Beacons for Allele Discrimination, Nature Biotechnol. 16: 49-53. Real-time multiplex assays utilizing PCR amplification have been demonstrated with TaqMan dual-labeled linear probes and the 5' nuclease detection process and, alternatively, with PCR amplification and molecular beacon probes, Tyagi. S. et al. (1998), supra; Vet, J. A. et al. (1999), Multiplex Detection of Four Pathogenic Retroviruses Using Molecular Beacons, Proc. Natl. Acad. Sci. USA 96: 6394-6399; El-Hajj, H. et al. (2001), Detection of Rifampin Resistance in *Mycobacterium tuberculosis* in a Single Tube with Molecular Beacons, J. Clin. Microbiol. 39: 4131-4137. Fluorescence-based multiplex assays currently are limited to about eight targets per sample by the need to minimize overlaps in emission spectra of fluorophores and, hence, are not expandable for use as highly multiplexed screening assays.

Highly multiplexed assays rely on spatial segregation of targets for signal resolution. Spatial segregation enables the use of coding schemes involving combinations of differently colored fluorophores (combinatorial coding), combinations of different amounts of each fluorophore (ratio coding), and both. One example of an assay with spatial segregation is fluorescence in situ hybridization, or FISH, for chromosomal analysis. Speicher et al. (1996), Karyotyping Human Chromosomes by Combinatorial Multi-fluor FISH, Nature Genet. 12: 368-375, for example, report the use of 27 probes combinatorially labeled using a set of six different fluorophores for analysis of chromosome spreads. Similarly, segregation of transcription sites in cell nuclei has enabled combinatorial coding utilizing multiple, singly labeled probes per site, as well as ratio coding. Singer, R. H., International (PCT) patent application WO 00/65094; Levsky, J. M. et al. (2002), Single-Cell Gene Expression Profiling, Science 297: 836-840. Another spatial-segregation probe technique is the use of multiplex probe arrays, including arrays on DNA chips. Schena, M. et al. (1995), Quantitative Monitoring of Gene Expression Patterns with a Complementary DNA Microarray, Science 20: 467-470; Gingeras, T. R. et al. (1998), Simultaneous Genotyping and Species Identification Using Hybridization Pattern Recognition Analysis of Generic *Mycobacterium* DNA Arrays. Genet. Res. 8: 435-448; Han et al. (2001), Quantum-Dot-Tagged Microbeads for Multiplexed Optical Coding of Biomolecules, Nature Biotechnol. 19, 631-635. Another segregation approach is the use if electrophoresis to separate ligated probe pairs of differing lengths. Tong, A. K. et al. (2001), Combinatorial Fluorescence Energy Transfer Tags for Multiplex Biological Assays, Nature Biotechnol. 19: 756-759. In that method, a variation of the oligonucleotide ligation assay ("OLA") for SNP detection, differently labeled probes are ligated to capture probes on a target, and the hybrids are immobilized, washed, released, separated from one another by electrophoresis, and read for each probes' fluorescent code, which is a combination of colors and ratios. Array methods and electrophoretic methods remain technically complex, requiring many separate steps, including amplification, hybridization, washing and analysis.

There is not currently available a homogeneous fluorescence hybridization assay that is suitable for use as a highly multiplexed screening assay, despite the need for such an assay. During suppressive treatment of the HIV-1 virus with protease inhibitors, for example, any of about 30 mutations is likely to proliferate over time and to require change in treatment. Hirsch, M. S. et al. (1998), Antiretroviral Drug Resistance testing in Adults with HIV Infection, JAMA 279: 1984-1991. Lacking a highly multiplexed screening assay, current practice is to sequence the virus in response to a patient's increase in viral load. Sequencing is made difficult by the fact that the arising mutant is not the only allele present. During initial diagnosis of a patient with particular symptoms, for example fever, there is available no highly multiplexed homogeneous assay to screen for an early indication of one of numerous possible infectious agents that may be the cause of the patient's symptoms.

An aspect of this invention is highly multiplexed homogeneous assays for screening samples for the presence of a target nucleic acid sequence from among at least ten, and as many as 60 or more, possible targets, utilizing conventional fluorescence detection equipment and techniques, and fluorescently labeled hybridization probes.

Another aspect of this invention is such screening assays that employ target amplification, optionally with real-time detection, that are capable of detecting small amounts of pathogens that may be found in otherwise sterile samples such as blood.

Yet another aspect of this invention is kits and oligonucleotide sets for carrying out particular screening assays according to this invention.

SUMMARY

Assays according to this invention are highly multiplexed assays suitable for screening. By "highly multiplexed," I mean that an assay is capable of detecting any of at least six, preferably at least 10, and in certain embodiments 30-60 and even more possible target sequences.

Assays according to this invention are homogeneous nucleic acid in vitro assays fluorescently labeled utilizing hybridization probes. By "homogeneous", I mean that nucleic acid targets are detected in solution without segregating targets spatially and without washing away unbound hybridization probes. Fluorescence signal is obtained from the reaction mixture itself. Certain preferred embodiments include target amplification by, for example PCR or NASBA, which enables detection of small amounts of pathogens in samples. When amplification is used, the reaction vessel, for example a microcentrifuge tube, is hermetically sealed to prevent contamination of the other samples being tested at the same time, samples not yet tested, equipment and workers.

Detection in assays according to this invention is by fluorescently labeled nucleic acid hybridization probes. Fluorescent labels, when stimulated emit radiation in the visible, ultraviolet or near infrared portions of the electromagnetic spectrum. Each probe is specific to one target among the multitude of possible targets being screened. If the goal and design of an assay are to distinguish among bacterial species, one will design a probe for a species, for example against a conserved region of *M. tuberculosis*, or design a probe that hybridizes to non-identical sequences of multiple strains of the same species. If the goal, on the other hand, is to distinguish among strains or mutant alleles, one will design each probe against a variable region to provide the necessary distinction and make the probe strain-specific. Preferred probes for use in this invention are molecular beacon probes, which may be made mismatch tolerant or mismatch intolerant, depending on the need of a particular assay. As is known in the art, choice of target sequence and probe design are balanced to minimize both false negatives and false positives.

Multiplex capability is achieved by combinatorial coding, with or preferably without added ratio coding, utilizing a panel of distinguishable fluorophores. In a combinatorial code, each code element is identified by its unique pattern of different labels, in this case colors. The combinatorial code includes up to four different fluorophores per code element. The different fluorophores are from a panel of at least four distinguishable fluorophores, more preferably a panel of 4-8 distinguishable fluorophores. The combinatorial code may be duplex coding in which the code elements comprise two colors, optionally enlarged by additional code elements of one color. The combinatorial code may by triplex coding in which the code elements comprise three colors, optionally enlarged by additional code elements of two colors (triplex code combined with a duplex code), and optionally enlarged by code elements of one color. The combinatorial code may be quadraplex coding in which the code elements comprise four colors, optionally enlarged by additional code elements of three colors, two colors or one color, or some combination thereof.

Rather than labeling individual probe molecules with multiplex colors to give the probe the pattern assigned to it as a code element, each probe is subdivided into the required number of portions, and each portion is labeled to emit a different color signal. The portions are then mixed to create a probe that, when hybridized to its target, will include the unique color signal pattern of the code element.

For the preferred highly quenched probes such as molecular beacon probes, each portion will emit a single color. For less preferred probes labeled with two different interacting fluorophores, such as 5'-nuclease probes, one option is to utilize a common short-wavelength fluorophore (which I call the "harvester" fluorophore), vary the long-wavelength fluorophores (which I call the "emitter" fluorophores), and detect the signal change in the latter. In that case, each portion will emit a signal in a different color. Another option is the reverse, namely, to use a common emitter fluorophore, vary the harvester fluorophores, and detect the signal change in the latter. In that case, each portion will also emit a signal in a different color, but for purposes of coding it is the harvester that becomes the detected emitter. However, a third option is to vary both fluorophores to permit detection of a ratio change in their emissions, so that the signal from one portion might be the ration a/b, the ratio from a second portion might be the ratio c/d, and the ratio from a third portion might be e/f, where a, b, c, d, e and f are distinguishable fluorophores. In this case the long-wavelength fluorophores are varied and can be considered to characterize the signal one obtains from any given probe portion. For ease of understanding, descriptions of combinatorial codes in this application and in the figures generally describe embodiments in which one detects for each probe portion the emission of a particular color, which can be characterized as the emitter fluorophore. It is to be understood that the teachings also apply to embodiments utilizing ratios, and persons skilled in the art will be able to apply the teachings to those embodiments.

If one begins with a panel of eight different fluorophores, for example, and chooses to subdivide each probe into four portions and to label each of the four portions with a different color, the codebook can include as many as 70 different combinations; if one begins with the same-sized panel of fluorophores but subdivides each probe into three portions and labels each of the three portions with a different color, the codebook can include as many as 56 different combinations; and if one begins with the same-sized panel of fluorophores but subdivides each probe into two portions and labels each of the two portions with a different color, the codebook can include as many as 28 different combinations. Four-color, three-color and two-color codes may be combined with each other and even with a one-color code, but my most preferred embodiments do not include such combinations. In ratio coding differing amounts of the same label are used for differentiation. Combinatorial codes according to this invention may be augmented with ratio coding, preferably integral ratio coding, that is, ratios of whole numbers such as 2:1, 3:1, 4:1 or 5:1, and vice versa. It is preferred that portions of molecular beacon probes be labeled with a non-fluorescent quencher and one signature-color fluorophore, most preferably without added ratio coding for reasons that will be explained.

As stated above, assays according to this invention are homogeneous detection assays. There is no segregation of targets. There is no separation of unbound probes from probes bound to their targets. Consequently, in assays according to this invention there must be a detectable signal change indicative of a probe hybridizing to its target. Preferred molecular beacon probes are highly quenched when free-floating at the detection temperature in the assay but change conformation and fluoresce when hybridized to their respective targets. Another type of probe whose fluorescence is restored by hybridization to its target and that is generally suitable for use in assays according to this invention is a "yin-yang" probe, a bimolecular probe labeled with a fluorophore on a target complementary strand and a quencher on a competing strand. Li, Q. et al. (2002), A New Class of Homogeneous Nucleic Acid Probes Based on Specific Displacement Hybridization, Nucleic Acids Res. 30: e5. Other probe-assay schemes result in a fluorescent signal change indicative of probes hybridizing to targets. In the 5'-nuclease detection process, end-labeled linear (or random-coil) probes with two different fluorophores interact by fluorescence resonance energy transfer (FRET) when free-floating but are cleaved during primer extension in a polymerase chain reaction (PCR) amplification, resulting in a signal change (emission from the shorter wavelength fluorophore increases, emission from the longer wavelength fluorophore decreases, and the ratio of the two changes accordingly). Livak, K. J. et al. (1995), supra. Another system, so-called LightCycler probes, works in the opposite manner. Each probe is a pair of fluorescently labeled linear oligonucleotides that hybridize adjacently on a target and interact by FRET, thereby producing a signal change (emission from the shorter wavelength fluorophore decreases, emission from the longer wavelength fluorophore increases, and the ratio of the two changes accordingly). Espy, M. J. et al. (2002), supra. For FRET systems, I refer to the shorter wavelength fluorophore as a "harvester" and the longer wavelength fluorophore as an "emitter". However, because the background resulting from FRET quenching is considerably higher than contact-mediated quenching that is commonly used in molecular beacon probes and yin-yang probes (Tyagi et al. (1998), supra; Marras, S. A. E. et al. (2002), Efficiencies of Fluorescence Resonance Energy Transfer and Contact-Mediated Quenching in Oligonucleotide Probes, Nucleic Acids Res. 30: e122), FRET quenching is not preferred for screening assays according to this invention. Assays according to this invention preferably employ probes that are quenched by contact-mediated quenching, such as molecular beacon probes or yin-yang probes. My most preferred probes are molecular beacon probes that include a non-fluorescent quencher. These probes are most preferred, not only because of their low background signal, but also because of their ease of design for a multiplex system. Bonnet, G. et al. (1998), Thermodynamic Basis of the Enhanced Specificity of Structured DNA Probes, Proc. Natl. Acad. Sci. USA 96: 6171-6176.

Assays according to this invention include, but are not limited to, embodiments that employ target amplification. Several exponential amplification techniques are well known. Among them are the polymerase chain reaction (PCR), which includes thermal cycling, and isothermal amplification schemes such as nucleic acid sequence-based amplification (NASBA), strand-displacement amplification (SDA), transcription-mediated amplification (TMA), rolling-circle amplification (RCA), and ramification amplification methodology (RAM). Amplification assay embodiments may utilize end-point detection or real-time detection. It is preferred to perform amplification in a sealed environment, for example sealed tubes, in the presence of the hybridization probes to minimize the possibility of cross contamination between samples that results from opening sample tubes.

While not limited by sample source, assays according to this invention advantageously may utilize human or animal samples sometimes referred to as being normally sterile, such as blood, tissue or spinal fluid. Such samples are advantageous as compared, for example, to sputum, stool or environmental samples, because they will contain fewer extraneous DNA sequences that could potentially interfere with amplification and detection. It is known that at least small amounts of many pathogens can be found in a patient's blood, even in septic syndromes resulting from bacterial infections. It is preferred to utilize normally sterile sources rather than non-sterile sources where a particular screening assay permits a choice.

Certain amplification assays according to this invention may advantageously take advantage of primers that amplify all or a number of nucleic acid targets being screened. When screening for mutations, it may be that numerous possible mutations occur in a particular variable nucleic acid sequence of interest, and one pair of primers flanking that region can be used to amplify all such possible mutations. Certain of these so-called "universal primers" bind to conserved regions of multiple species and are used for amplifying numerous targets, for example genes of various bacteria. See, for example, Kox, L. F. F. et al. (1995), PCR Assay Based on DNA Coding for 16S rRNA for Detection and Identification of Mycobacteria in Clinical Samples. J. Clin. Microbiol. 33: 3225-3233; Iwen, P. C. et al. (1995), Evaluation of Nucleic Acid-Based Test (PACE 2C) for Simultaneous detection of *Chlamydia trachomatis* and *Neisseria gonorrhoeae* in Endocervical Specimens, J. Clin. Microbiol. 33: 2587-2591; Yang, S. et al. (2002), Quantitative Multiprobe PCR Assay for Simultaneous Detection and Identification to Species Level of Bacterial Pathogens, J. Clin. Microbiol. 40: 3449-3454; Schonhuber, W. et al. (2001), Utilization of mRNA Sequences for Bacterial Identification, BMC Microbiol. 1: 2; Wong, R. S. and Chow, A. W. (2002), Identification of Enteric Pathogens by Heat Shock Protein 60 kDa (HSP 60) Gene Sequences, FEMS Microbiol. Lett. 206: 107-113. One pair, more likely two or three pairs, of primers may suffice for particular screening assays.

This invention includes assay kits for performing particular multiplex screening assays according to this invention. Kits include at least the intended complement of detection probes. We refer to collections of oligonucleotides as "oligonucleotide sets." When the assay is an amplification assay, for example a PCR assay, the oligonucleotide sets preferably also include the primers needed for amplification. They may also include any amplifiable control sequence. Kits may include additional assay reagents such as enzymes, amplification buffer and, if desired, sample preparation reagents for isolation of nucleic acids; that is, up to all reagents needed for performing the assay, from sample preparation through detection.

Fluorescence-based screening assays of this invention are generally adaptable to detection instruments, which may include thermal cycling capability. Instruments may use a single-wavelength source or a multi-wavelength source, for example a white light combined with selectable filters, multiple laser sources or multiple light-emitting diode sources. Detection instruments vary in their ability to distinguish emissions from multiple fluorophores, which needs to be taken into account when selecting fluorophore panels for a particular assay. In preferred embodiments of assays according to this invention, emissions from fluorophores for each probe are balanced in intensity such that intensities from the subdivided portions are closely spaced, which aids identification. Fluorophores vary in intensity, target sequences vary in accessibility for probe hybridization, and instruments may vary in their responses to different wavelengths. Relative amounts of portions may be varied to achieve balance. Where possible, it is preferred that all portions for all probes be balanced to further aid in identification. The results of these assays can be automatically decoded and interpreted by computer programs in real time, enabling the assays to be highly accurate, and to be carried out in an automated, high-throughput fashion in clinical diagnostic settings.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a table showing the numbers of distinguishable combinations obtained using two or three colors per probe and panels of 4-8 distinguishable fluorophores.

FIGS. 6a and 6b contain tables that show the effect of alternative probe coding schemes for detecting ten different possible targets in a sample, utilizing probes that are each labeled with three different colors of equal fluorescence intensity from a palette of five different fluorophores, on the results that would be obtained for every one of the 45 possible combinations of two different targets that could be present at the same concentration in a sample being tested.

DETAILED DESCRIPTION

Figure 2:
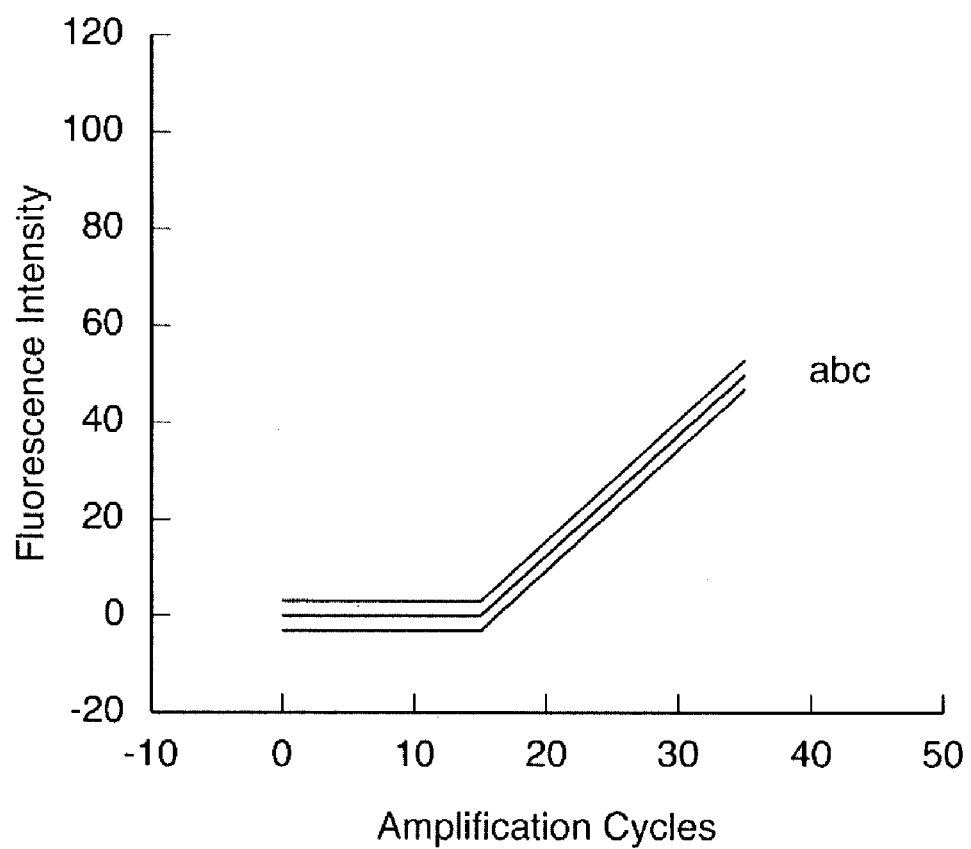
FIG. 2 illustrates fluorescence emissions of a real-time amplification assay in which a single target sequence is present in the sample being tested (out of many possible target sequences that the assay is designed to detect) and one probe (labeled with three different colors of equal fluorescence intensity) among the many different probes in the assay mixture binds to the amplified target sequence.

FIG. 1 is a table presenting certain combinatorial coding schemes useful in this invention. The top portion of the table presents the number of codes obtained by having each probe differently labeled with two different fluorophores from panels of 4, 5, 6, 7 or 8 fluorophores. If the panel includes eight fluorophores, there are 28 possible codes. The bottom portion of the table presents the number of codes obtained by having each probe labeled with three different fluorophores from the same panels of 5, 6, 7 or 8 fluorophores. If the panel includes eight fluorophores, there are 56 possibilities. Assays according to this invention utilize two or three (and sometimes four) differently labeled portions of each probe and a panel of fluorophores of sufficient size to permit at least six differently coded probes. This may be accomplished, for example, by combining the two portions of the table, that is, using both codes of two colors and codes of three colors. For example, probes may be subdivided into three portions for use with a panel of five fluorophores, providing up to ten differently coded probes, as outlined in the bottom portion of the table, and additional probes may be subdivided into two portions for use with a panel of five fluorophores, providing up to ten additional differently coded probes, as outlined in the top portion of the table. In this manner, as many as 20 differently coded probes can be combined in the same assay mixture.

Assays according to this invention utilize one probe (which may be a single-molecule probe, such as a molecular beacon probe or a TaqMan probe, or a bi-molecular probe, such as a yin-yang probe or a LightCycler probe pair) for each target. Coding is achieved, except for a code element represented by a single color, by subdividing probes into portions and labeling the portions according to a combinatorial code or combinatorial-plus-ratio code from a panel of at least four, preferably 5-8, distinguishable fluorophores. Utilizing our preferred molecular beacon probes for purposes of illustration, each probe portion is designed to have a different color signature. Certain of the probes may be wavelength-shifting probes, that is, probes in which one arm is labeled with a quencher and the other arm is labeled with a FRET pair comprising a "harvester" fluorophore to absorb energy from the stimulating light source and transfer that energy to an "emitter" fluorophore that fluoresces strongly at its own characteristic longer wavelength spectrum when the probe is in its open configuration. We utilize wavelength-shifting probes with instruments that employ a single wavelength source that is not highly absorbed by fluorophores that emit visible fluorescence at longer wavelengths, for example, Texas Red. See Tyagi, S. et al. (2000), Wavelength-Shifting Molecular Beacons, Nature Biotechnol. 18: 1191-1196; El-Hajj, H. et al. (2001), supra. It is also possible to utilize one fluorophore to quench another fluorophore by contact-mediated quenching. This creates two additional possibilities. First, a fluorophore that has relatively low emission in the system being used could be placed on each arm so that the fluorophores quench one another when the probe is closed but both fluoresce with the same color, increasing its intensity, when the probe is hybridized to its target and open. This technique can be used to add ratio coding to a combinatorial code. Second, one portion of a probe can carry two code elements (colors) by placing different fluorophores on the two arms, so that the fluorophores quench one another when the probe is closed but each fluoresces in its own characteristic emission spectrum when the probe is hybridized to its target and open. This can be used to combine two portions into one and thereby reduce the number of different portions needed for a two-color, three-color or four-color code element. It is equivalent to having separate portions. Because quenching by non-fluorescent quenchers is more efficient than quenching by fluorophores and because having two emitting fluorophores on the same molecule removes the option to balance their intensities by means of relative concentration, preferred embodiments of this invention utilize a non-fluorescent quencher on one arm of molecular beacon probes. Dabcyl is a preferred quencher, as is Black Hole Quencher No. 2.

"Codebooks" useful in this invention utilize four colors per probe, three colors per probe, two colors per probe, or combinations of four, three or two colors per probe, with or without single-color probes. Preferred codebooks utilize either only four colors per probe, only three colors per probe or only two colors per probe. The reason these are preferred is that the appearance of, for example, one color arising at a particular PCR cycle signals that an error has been made in assay preparation. If single-color probes are used, such an error is not obvious. In some embodiments of this invention, combinatorial coding may be supplemented with ratio coding to increase the number of code elements or possibilities. Preferred ratios are integral, from 5:1 to 1:5, preferably from 3:1 to 1:3. Ratio coding is most appropriate for screening assays in which it is highly likely that only one target will be found. The reason for this is that when the code is strictly combinatorial and two or more targets are present, changes in intensity levels are helpful for resolving ambiguities that may arise in analysis of the emission spectrum. Therefore, preferred assays that are not highly likely to find only one target utilize strictly combinatorial coding.

Various fluorophores can be included in panels of fluorophores. Certain fluorophores have relatively narrow emission spectra, for example, Vic, Alexa 488, and quantum dots (Gao et al. (2002), Quantum-Dot Nanocrystals for Ultrasensitive Biological Labeling and Multicolor Optical Encoding, J. Biomed. Opt. 7, 532-537), making them particularly useful for highly multiplexed assays utilizing panels of more than six fluorophores.

Oligonucleotide probes, including molecular beacon probes, are conveniently prepared by solid-phase DNA synthesis on, for example, an Applied Biosystems 394 DNA/RNA synthesizer. DNA nucleotides or RNA nucleotides may be used, including modified nucleotides such as 2'-O-methylribonucleotides, which yield strands resistant to cleavage. Our preferred method of molecular beacon synthesis starts with controlled-pore glass columns containing the quencher dabcyl for incorporation at the 3' end of the probe. These columns are available from Biosearch Technologies (Novato, Calif., USA). Our preferred method of incorporating fluorophores at the 5' end of the probe is to utilize thiolmodifier phosphoramidites or aminomodifier phosphoramidites so that iodoacetylated fluorophore derivatives can be coupled to the 5'-thiol groups and succinimidyl esters of fluorophores can be coupled to the 5'-amino groups. For tetrachlorofluorescein, our practice is to incorporate directly a tetrachlorofluorescein phosphoramidite. For wavelength-shifting probes a non-terminal fluorophore is required. We have used fluorescein phosphoramidites to incorporate internal fluorescein moieties for this purpose. Our molecular beacon probe synthesis includes probe purification by gel exclusion chromatography through NAP-5 Sephadex columns, followed by HPLC through a reverse-phase column such as the C-18 column marketed by Waters. Finally, probes are precipitated with ethanol and dissolved in 100 µl Tris-EDTA buffer. Molecular beacon probes should have a signal-to-noise ratio of at least 25, preferably closer to 100, keeping in mind that for a triplet code, for example, each fluorophore will be common to 30-60% of the probes.

As indicated above, the probes are subdivided into two, three or four portions for labeling and use. It is advantageous that the various portions of a probe, and where possible all portions in the assay, produce roughly the same signal intensity. Accordingly, our preferred assays and kits have portions "balanced" for that purpose. By "balanced" I mean that the fluorescence intensities of the signals from the different portions are generally within 20% of one another, most preferably within 5%. The fluorescence intensity produced by a particular probe portion, for example a molecular beacon probe portion, will depend on the intrinsic properties of its emitter fluorophore (and, if it is a wavelength-shifting molecular beacon probe, also its harvester fluorophore), the nature of the target, as some targets accept probes more readily than others, and quite possibly on the instrument utilized for detection. By testing a probe against its target in the assay on the instrument to be used, the amounts of the portions relative to one another can be adjusted to produce balanced signals. I prefer further that all portions of all of the combinatorially labeled probes be balanced. After the portions of each probe are balanced, the amounts of the probes relative to one another can be adjusted to produce balanced signals. It is possible to adjust signal readings by adjusting the detection instrument rather than the amounts of the portions of each probe to account for differences in the fluorophores and the instrument. For example, if a probe with three portions labeled a, b, c produces relative intensities with equal volumes of each portion of 1.0, 1.5 and 3.0, respectively, the instrument could be programmed to multiply readings from portion "a" by three, from portion "b" by two, and from portion "c" by one. Then only the relative amounts of the probes would have to be balanced. My preference, however, is to adjust the portion amounts rather than the instrument. Utilizing balanced emissions makes interpretation by a human observer significantly easier, as one can see immediately whether or not three colors, for example, indicate a particular code element.

Assays according to this invention are highly multiplexed. While not limited as to sample source, the assays are particularly applicable for use with samples from human or other animal body sites that are considered sterile, such as blood, tissue and cerebral spinal fluid. Non-sterile specimens, such as sputum or stool, are likely to have nucleic acids from a variety of sources and are more difficult to screen for that reason. Pathogens generally infect the blood stream to at least a small degree. However, nucleic acid amplification assays require minimal amounts of target sequence in the sample. For example, Kane et al. compared blood culturing to PCR assays utilizing "universal' bacterial primers to diagnose bacterial infection in critically ill surgical patients. Kane, T. D. et al. (1998), The Detection of Microbial DNA in Blood: a Sensitive Method for Diagnosing Bacteremia and/or Bacterial Translocation in Surgical Patients. Ann. Surg. 227: 1-9. Whereas blood cultures were positive for only 14% of the samples, the PCR assays were positive for 64%.

For embodiments employing amplification, such as PCR or NASBA, primers are required for the various possible targets. Primer design is known in the art. Primers can be tested with other primers and then with probes to check for undesired interactions. It is important that primers, and to a lesser extent probes, not interact in multiplex reactions. A type of high-specificity primer useful in this invention is disclosed in published international patent application WO 00/71562. Such primers form hairpin stems that significantly reduce undesired hybridizations. We have decreased primer interactions by utilizing such high-specificity primers, taking care to ensure that the melting temperature ($T_m$) of the stem is approximately 6° C. above the primer annealing temperature utilized in the assay. We have constructed two pairs of universal primers that together amplify a segment of the 16s ribosomal RNA gene of many bacterial species. One pair includes 5'-TGACGACAACCATGCACC-3' (SEQ. ID NO. 1) and 5'-ATGTGGTTTAATTCGAAGCAA-3' (SEQ. ID NO. 2) to amplify target regions in *B. anthracis* and related gram-positive bacterial. The other pair includes 5'-<u>GTGGAC</u>TTAGATACCCTGGTA<u>GTCCAC</u>-3' (SEQ. ID NO. 3) and 5'-GCGTTGCATCGAATTAA-3' (SEQ. ID NO. 4), which amplify target regions in several important gram-positive bacteria and gram-negative bacteria. The underlined sequences of the third identified probe are hairpin-forming sequences added to reduce undesired hybridizations by this primer.

Amplification assays with real-time detection can be performed on a variety of instruments that utilize different techniques for exciting fluorophores and detecting emissions. Excitation can be by lasers, white light coupled with filters, or light-emitting diodes. In addition, the assay instrument may utilize a synchronous scanning mode, in which narrow excitation and emission wavelengths are continuously varied, while maintaining a fixed wavelength difference between them. Lee et al. (1999), Seven-Color, Homogeneous Detection of Six PCR Products, Biotechniques 27, 342-349. The choice of instrumentation may affect the number of different fluorophores that can be included in a panel.

Screening assays according to this invention, including but not limited to real-time amplification assays, may be positive for a single target, in which case the target is identifiable by its unique signature, preferably its unique color signature but possibly by its color-plus-intensity signature. On occasion two or even more than two targets may be present in a sample. Deciphering the spectrum in such a case may take advantage of the fact that, although the absolute fluorescence of a probe is dependent on target concentration, the fluorescence ratios of two probe portions hybridizing to the same target will be independent of target concentration. Taking the case of strictly combinatorial coding utilizing three-color codes wherein the intensities of the portions have been balanced, assume that two targets are present. If the targets share no color, there will result six colors. However, because equal concentrations of the two targets in the sample are highly unlikely, direct probing of the sample is likely to result in three colors of one intensity and three colors of a second intensity, thereby identifying the two targets. If the assay, on the other hand, is a real-time amplification assay, the times at which signals rise above background, for example the threshold cycle ($C_T$) of a PCR reaction, are likely to differ, leading to two groups of three colors, each group arising at a different time, thereby identifying the two targets.

If the codes assigned to the probes for the two targets share a color, in an assay based on directly probing the nucleic acids in a sample, the fluorescence intensity for that color will not match the fluorescence intensity for the other colors. Rather it will be a combination from two targets and will stand out from the level of the other colors, thereby identifying it as the color in common. If the assay, on the other hand, is a real-time amplification assay, three colors will come up together as signal from the more abundant target. When the second threshold for the less abundant target is reached, two more colors will come up together and the intensity curve for the common color will change slope to a higher value, thereby identifying it as the color in common.

Taking the case where ratio coding is also used, assume one color is common to two targets, but its intensity ratio for the more abundant target is 2:1 as compared to the other portions for that target. In a real-time amplification assay three colors will rise above background as the first threshold is reached, but one color (the common color) will have a higher slope than the other two colors. Nonetheless, when the second threshold is reached, the intensity curve of the common color will change slope to a higher value, signifying its commonality.

When two different target species are present in the sample at the same concentration, the colors encoding each probe will appear at the same time. In some instances of this situation it may not be possible to unambiguously identify each code. In such an instance a repeat assay utilizing an alternative coding scheme for the targets, should in almost all cases resolve the ambiguity.

EXAMPLE 1

In this example, a real-time PCR amplification assay is carried out on DNA isolated from a normally sterile blood sample suspected of containing an infectious bacterium. The sets of primers that are present in the reaction mixture enable the amplification of a segment of the 16s ribosomal RNA gene that is present in all of the bacterial species that are suspected of possibly being present in the blood sample. A multiplicity of molecular beacon probes is present in the assay, one for each of the suspected bacterial target species. Each different molecular beacon possesses a universal quencher moiety (dabcyl) covalently linked to its 3' end. Each different species-specific molecular beacon probe is labeled combinatorially according to this invention with a unique set of three differently colored fluorophores. These fluorophores are covalently linked to the 5' end of each oligonucleotide. For every species-specific probe that is present in the assay mixture, the abundance of each of the three differently colored oligonucleotides that together make up the species-specific probe is adjusted prior to performing the assay so that the fluorescence intensity of each of the three colors of that probe will be approximately the same when measured in the assay instrument used to carry out the assay. FIG. 2 is a plot of results that will be obtained in this assay. The "x" axis represents the number of amplification cycles performed by the time that each measurement of fluorescence is made. This measurement is made automatically by the assay instrument in a manner that permits the fluorescence intensity of each of the differently colored fluorophores that are used to label the probes to be measured. The "y" axis represents the fluorescence intensity due a particular colored fluorophore. Measurements are taken during the annealing phase of each amplification cycle. Measurements are taken in real time during each amplification cycle throughout the course of the amplification. The fluorescence intensity of each of the differently colored fluorophores used to label the probes is plotted as a function of the number of amplification cycles completed.

In the experiment shown in FIG. 2, a signal appears that is sufficiently intense to be detected above the background fluorescence after a particular number of cycles of amplification have been carried out. The amplification cycle at which this occurs is known as the "threshold cycle", generally abbreviated as "$C_T$". The signal that appears after the threshold cycle consists of three different colors (a, b, and c).

This signal rises in a linear fashion as more cycles of amplification are completed. The set of three colors that appear together in combination identify which bacterial species is present in the blood sample. The abundance of the species in the sample is determined from the threshold cycle at which the signal arises. The threshold cycle is inversely proportional to the logarithm of the number of target molecules in the sample

EXAMPLE 2

Figure 3:
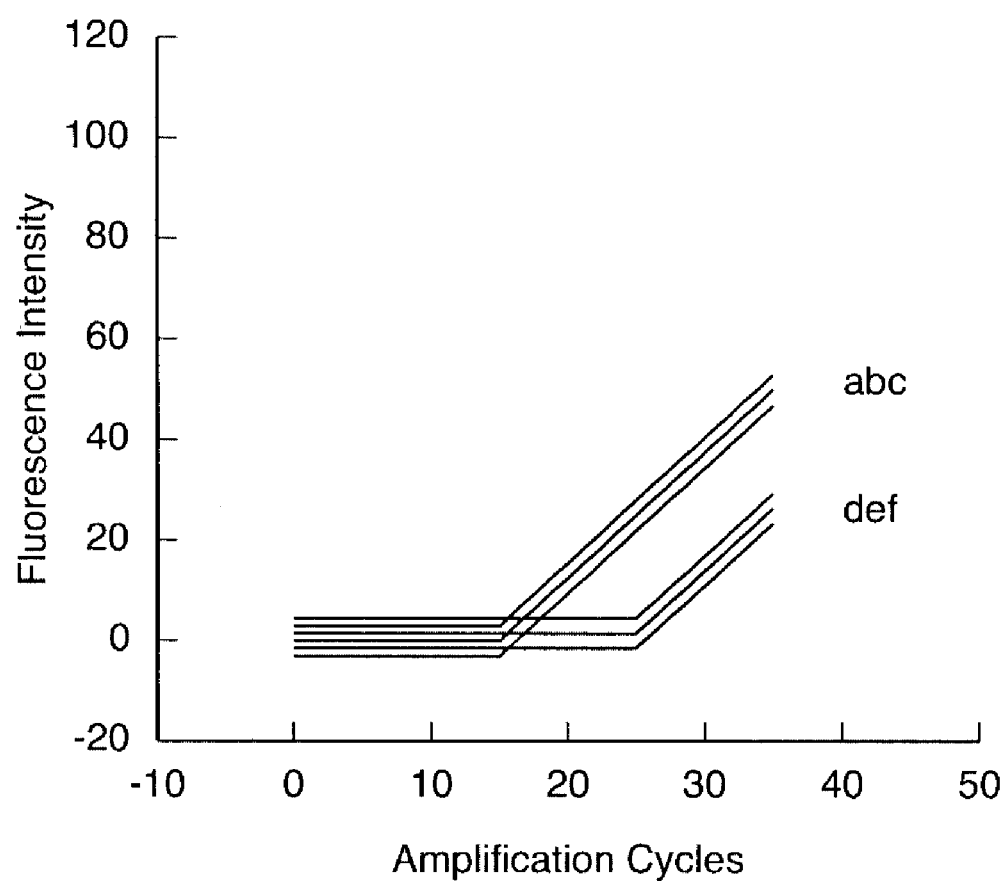
FIG. 3 illustrates fluorescence emissions of a real-time amplification assay in which two different target sequences are present at different concentrations in the sample being tested and two probes (each labeled with a different combination of three different colors of equal fluorescence intensity, no color being shared by both probes) bind to the amplified target sequences.

In this example, an assay is carried out in the same manner and for the same purpose as the assay described in Example 1. The results that will be obtained in this experiment are shown in FIG. 3. Two different signals occur, one (consisting of colors a, b, and c) appears early in the reaction, and the other (consisting of colors d, e, and f) appears later in the reaction. This result indicates that two different bacterial species are present in the sample, one (identified by colors a, b, and c) is relatively abundant, and the other (identified by colors d, e, and f) is relatively rare and therefore requires more cycles of amplification before there is sufficient amplified product for the fluorescence signal due to the hybridization of the species-specific probe to be seen above the background fluorescence. The unique set of colors in each of the two signals unambiguously identifies each of the two bacterial species that are present in the sample.

EXAMPLE 3

Figure 4:
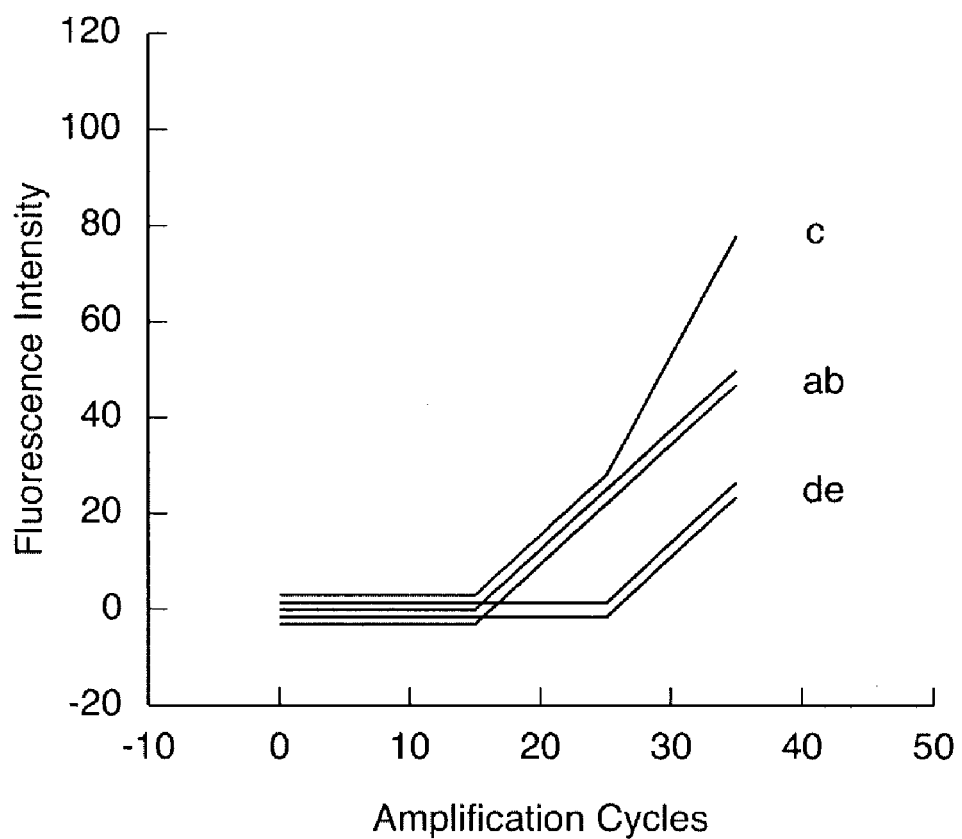
FIG. 4 illustrates fluorescence emissions of a real-time amplification assay in which two different target sequences are present at different concentrations in the sample being tested and two probes (each labeled with a different combination of three different colors of equal fluorescence intensity, one color being shared by both probes) bind to the amplified target sequences.

In this example, an assay is carried out in the same manner and for the same purpose as the assay described in Example 1. The results that will be obtained in this experiment are shown in FIG. 4. Two different signals occur, one (consisting of colors a, b, and c) appears early in the reaction, and the other (consisting of colors d and e) appears later in the reaction. In addition, the slope of the curve showing the fluorescence intensity of color "c" increases after the threshold cycle at which the later signal (consisting of colors d and e) occurs. This result indicates that two different bacterial species are present in the sample, one (identified by colors a, b, and c) is relatively abundant, and the other (identified by colors c, d, and e) is relatively rare and appears later. The increase in the slope of the curve showing the fluorescence intensity of color "c" is due the contributions of "c" fluorescence from probes binding to amplified segments of the DNA from the rare bacterial species being added the "c" fluorescence from probes binding to amplified segments of the DNA from the abundant bacterial species. Even though the three-color codes for each of the two bacterial species that are present in the sample have one color in common, the occurrence of the two species at different concentrations in the sample enables the signals from each species to be distinguished from one another. In general, when two (or even three) species are simultaneously present in a clinical sample, each will occur at a different concentration, and the coded signal due to the presence of each of the bacterial species can be distinguished from the signals due the other species in the sample.

EXAMPLE 4

This example illustrates how unambiguous results can be obtained even though two different species are present in a sample at approximately the same concentration. The assay described in this example is carried out in the same manner and for the same purpose as the assay described in Example 1. In this experiment, the probes present in the assay mixture are designed to detect ten different bacterial species (designated species 0, 1, 2, 3, 4, 5, 6, 7, 8, and 9). Three-color codes are used to label each of the ten probes, from a palette of five differently colored fluorophores (designated a, b, c, d, and e). For every species-specific probe that is present in the assay mixture, the abundance of each of the three differently colored oligonucleotides that together make up the species-specific probe is adjusted prior to performing the assay so that the fluorescence intensity of each of the three colors of that probe will be approximately the same when measured in the assay instrument used to carry out the assay. For this assay, the following coding scheme (which I call the "first ternary color codebook") is used:

| probe for species 0 | abc |
| probe for species 1 | abd |
| probe for species 2 | abe |
| probe for species 3 | acd |
| probe for species 4 | ace |
| probe for species 5 | ade |
| probe for species 6 | bcd |
| probe for species 7 | bce |
| probe for species 8 | bde |
| probe for species 9 | cde |

Figure 5:
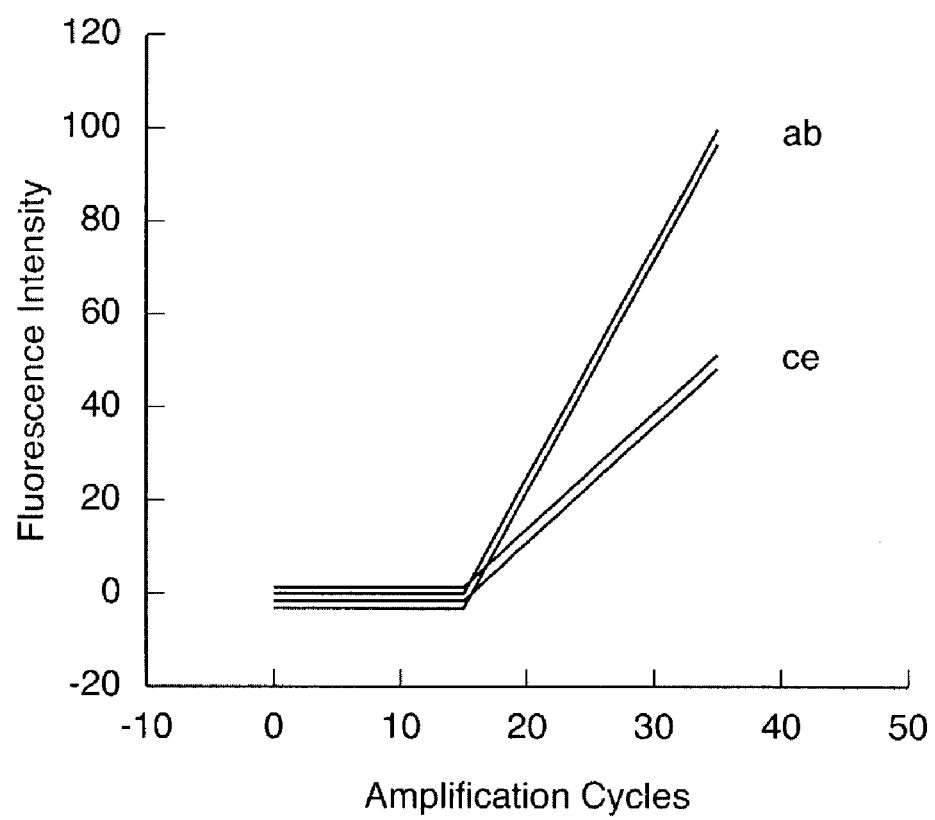
FIG. 5 illustrates fluorescence emissions of a real-time amplification assay in which two different target sequences are present at the same concentration in a sample being tested, and two probes (labeled according to the first ternary color codebook shown in FIG. 6a) share two colors, leading to unambiguous interpretation of the results.

The results that will be obtained in the experiment carried out with probes labeled according to this codebook are shown in FIG. 5. A signal consisting of four different colors (a, b, c, and e) arises at the same threshold cycle. The slope of the curves for two of the colors (a and b) is twice as high as the slope of the curves for the other two colors (c and e). This result indicates that two different bacterial species are present in the sample at approximately the same concentration, and that the three-color codes of their respective probes have two colors in common. Since the slope of the curves for colors "a" and "b" is approximately twice as high as the slope of the curves for colors "c" and "e", colors "a" and "b" are components of the codes for both bacterial species that are present in the sample. The conclusion to be drawn from these results is that one of the probes that bound to amplified target sequences was encoded "abc" and the other probe that bound to amplified target sequences was encoded "abe". By comparing these results with the coding scheme in the first ternary color codebook (shown above), "abc" is seen to be the code for bacterial species "0" and "abe" is seen to be the code for bacterial species "2". Thus, the results unambiguously indicate that the sample contains species "0" and species "2" in approximately equal concentration.

EXAMPLE 5

This example illustrates how ambiguous results can sometimes be obtained when two different species are present in a sample at approximately the same concentration. The assay described in this example is carried out in the same manner and for the same purpose as the assay described in Example 4. The probes used in this assay utilize the first ternary color codebook (shown in Example 4).

FIG. 6a contains a two-part table (based on the first ternary color codebook) that shows the results that should occur when two different species are present in a sample at the same concentration for each of the 45 combinations of two species that are possible. In 30 of these combinations four colors arise, two at a higher rate of fluorescence intensity increase (identified by underlined letters) and two at a lower rate of fluorescence intensity increase (identified by letters that are not underlined). Each of these 30 combinations is unique within the table, therefore providing an unambiguous result.

Figure 7:
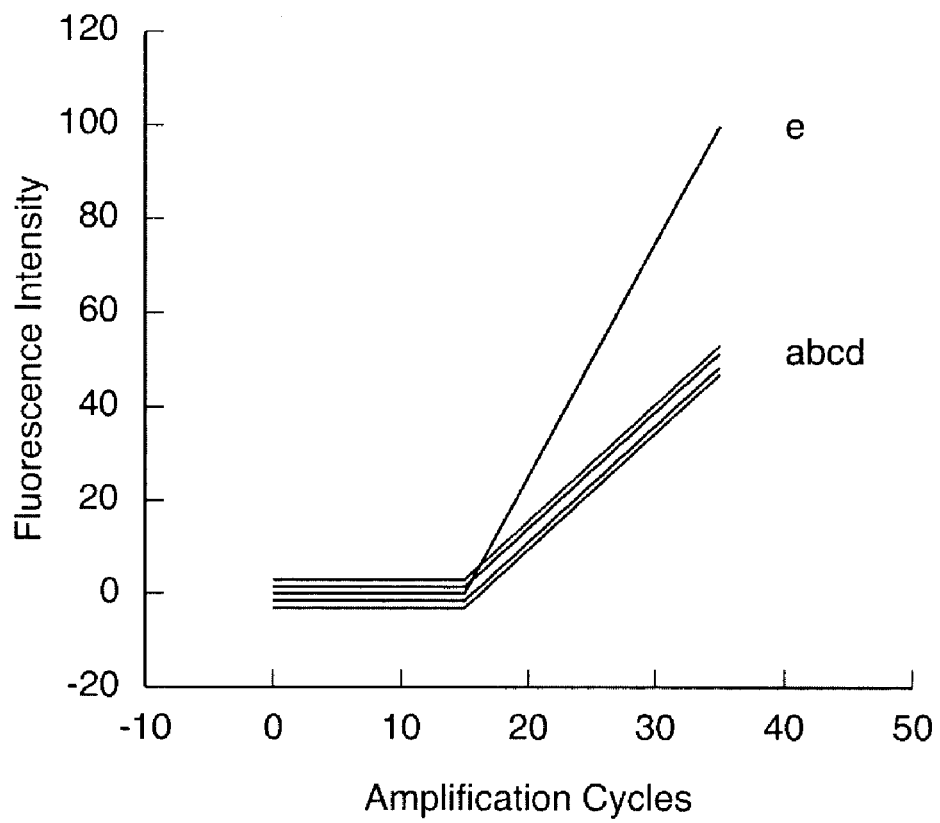
FIG. 7 illustrates fluorescence emissions of a real-time amplification assay in which two different target sequences are present at the same concentration in a sample being tested, and two probes (labeled according to the first ternary color codebook shown in FIG. 6a) share one color, leading to an ambiguous result.

However, from an examination of FIG. 6a it can be seen that in 15 of the 45 possible combinations of two different species that can be present in a sample at the same concentration five colors arise, one at a higher rate of fluorescence intensity increase (identified by an underlined letter) and four at a lower rate of fluorescence intensity increase (identified by letters that are not underlined). These combinations, however, are not unique. For example, the code "abcde" occurs three times in the upper table: once for the combination of species "2" and "9", a second time for the combination of species "4" and "8", and a third time for the combination of species "5" and "7". An example of an experiment that yields such an ambiguous outcome is shown in FIG. 7. The results of this assay show five colors arising at the same threshold cycle (a, b, c, d, and e), one color of which (e) increases in intensity at twice the rate as the other four colors.

EXAMPLE 7

Figure 8:
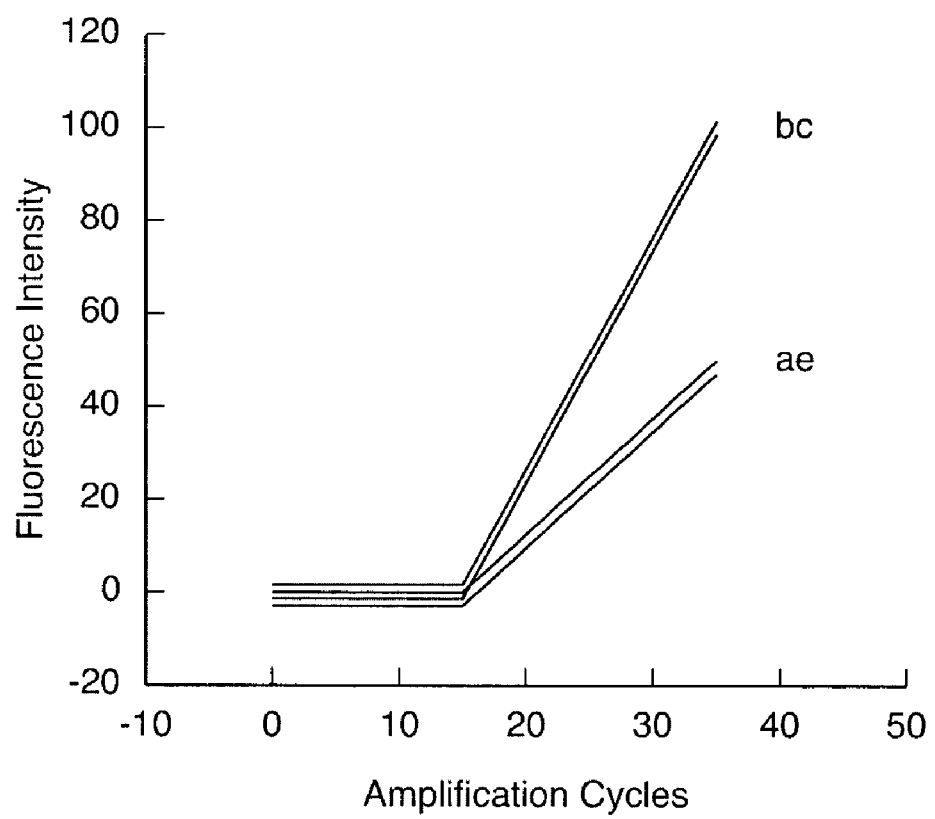
FIG. 8 illustrates fluorescence emissions of a real-time amplification assay in which the same sample used in the assay shown in FIG. 7 is retested using probes labeled according to the second ternary color codebook shown in FIG. 6b, providing an example of how a second assay utilizing an alternative coding scheme can resolve ambiguous results.

The ambiguities inherent in results such as those shown in FIG. 7 can be resolved by repeating the assay with the same probes encoded by an alternative coding scheme. For example, the assay giving results shown in FIG. 8 is carried out on the same sample used to obtain the results shown in FIG. 7, except that the probes are encoded by the following alternative coding scheme (which I call the "second ternary color codebook"):

| probe for species 0 | cde |
| probe for species 1 | bde |
| probe for species 2 | bce |
| probe for species 3 | bcd |
| probe for species 4 | ade |
| probe for species 5 | ace |
| probe for species 6 | acd |
| probe for species 7 | abe |

-continued

| probe for species 8 | abd |
| probe for species 9 | abc |

FIG. 8 shows the results that will be obtained from an assay on the same sample used in the experiment shown in FIG. 7, except that the probes are encoded according to the second ternary color codebook. A signal consisting of four different colors (a, b, c, and e) arises at the same threshold cycle. The slope of the curves for two of the colors (b and c) is twice as high as the slope of the curves for the other two colors (a and e). Since the slope of the curves for colors "b" and "c" are approximately twice as high as the slope of the curves for colors "a" and "e", colors "b" and "c" are present in the codes for both bacterial species that are present in the sample. The conclusion drawn from these results is that one of the probes that bound to amplified target sequences is encoded "abc" and the other probe that bound to amplified target sequences is encoded "bce". By comparing these results with the coding scheme in the second ternary color codebook (shown above), "bce" is seen to be the code for bacterial species "2" and "abc" is seen to be the code for bacterial species "9". Thus, the results shown in FIG. 8 resolve the ambiguity posed by the results shown in FIG. 7, unambiguously indicating that the sample contains species "2" and species "9" in approximately equal concentration.

FIG. 6b shows the results that should occur for all 45 different combinations of two different bacterial species in a sample at approximately the same concentration when the probes are encoded according to the second ternary color codebook. A comparison of the two-part table in FIG. 6a with the two-part table in FIG. 6b shows that all 45 possible combinations of two different bacterial species can be unambiguously identified by carrying out a second assay with alternatively coded probes when it is necessary to resolve ambiguities arising from the first assay.

A number of embodiments of the invention have been described. Nevertheless, it will be understood that various modifications may be made without departing from the spirit and scope of the invention. Accordingly, other embodiments are within the scope of the following claims.

What is claimed is:

1. A highly multiplexed homogeneous in vitro assay to screen a sample for the presence of any of a minimum of six different nucleic acid targets comprising
  a) contacting the sample with a set of at least six fluorescent hybridization probes, each one specific for a different one of said nucleic acid targets, wherein
    i) each probe in said set is subdivided into the same number of portions, said number being in the range of from two to four,
    ii) each portion of each subdivided probe is labeled with a different emitter fluorophore from a panel of at least four spectrally differentiable fluorophores,
    iii) each probe in said set has a unique color signal pattern, and
    iv) hybridization of each probe leads to a detectable fluorescence signal change indicative of the color pattern of the labeling of its portions;
  b) stimulating the fluorophores present in the sample; and
  c) detecting changes in emissions signals from said fluorophores without spatially segregating the nucleic acid targets from one another to detect the color pattern of one of said probes so as to identify which target is present.

2. The assay according to claim 1 further comprising exponentially amplifying said nucleic acid targets.

3. The assay according to claim 2 wherein changes in emission signals are detected in real time during amplification.

4. The assay according to claim 1 wherein the relative amounts of the portions of each probe are adjusted relative to one another to provide balanced signal changes.

5. The assay according to claim 1 wherein said set of probes additionally includes at least one probe that is ratio coded.

6. The assay according to claim 1 wherein said probes are quenched probes whose fluorescence is restored by hybridization to their targets.

7. The assay according to claim 6 wherein said probes are molecular beacon probes having a non-fluorescent quencher on one arm and an emitter fluorophore on the other arm.

8. The assay according to claim 7 wherein the fluorescence intensities of the portions of each probe are balanced relative to one another.

9. The assay according to claim 7 further comprising exponentially amplifying said nucleic acid targets in the presence of said probes and detecting increases in fluorescence from emitter fluorophores in real time.

10. The assay according to claim 9 wherein said panel of fluorophores consists of from four to eight differentiable fluorophores, wherein the relative amounts of the portions of each probe are adjusted relative to one another to provide balanced fluorescence emissions.

11. The assay according to claim 10 wherein the relative amounts of all portions of all probes are adjusted relative to one another to provide balanced fluorescence emissions.

12. The assay according to claim 1 further comprising at least one additional probe that is subdivided into fewer portions than are the probes in said set of probes, wherein said at least one additional probe has a unique color pattern.

* * * * *

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
tgacgacaac catgcacc                18

<210> SEQ ID NO 2
<211> LENGTH: 21
<212> TYPE: DNA
<213> ORGANISM: Artificial Sequence
<220> FEATURE:
<223> OTHER INFORMATION: primer -continued

```
<400> SEQUENCE: 2
atgtggttta attcgaagca a                                             21

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
gtggacttag ataccctggt agtccac                                       27

<210> SEQ ID NO 4
<211> LENGTH: 17
<212> TYPE: DNA
<213> ORGANISM: Artificial Sequence
<220> FEATURE:
<223> OTHER INFORMATION: primer

<400> SEQUENCE: 4
gcgttgcatc gaattaa                                                  17
```